(12) United States Patent  (10) Patent No.: US 9,358,080 B2
Clark  (45) Date of Patent: Jun. 7, 2016

(54) DENTAL SEPARATOR RING

(71) Applicant: David J. Clark, Lakewood, WA (US)

(72) Inventor: David J. Clark, Lakewood, WA (US)

( * ) Notice: Subject to any disclaimer, the term of this patent is extended or adjusted under 35 U.S.C. 154(b) by 0 days.

(21) Appl. No.: 13/850,910

(22) Filed: Mar. 26, 2013

(65) Prior Publication Data

US 2013/0252199 A1 Sep. 26, 2013

Related U.S. Application Data

(60) Provisional application No. 61/615,648, filed on Mar. 26, 2012.

(51) Int. Cl.
A61C 5/04 (2006.01)
A61C 5/12 (2006.01)

(52) U.S. Cl.
CPC .................................... A61C 5/125 (2013.01)

(58) Field of Classification Search
CPC ........... A61C 5/127; A61C 5/125; A61C 5/12
USPC ........................ 433/139, 149, 153, 155, 158
See application file for complete search history.

(56) References Cited

U.S. PATENT DOCUMENTS

| | | | | |
|---|---|---|---|---|
| 396,537 | A * | 1/1889 | Browne | 433/158 |
| 943,353 | A * | 12/1909 | Ivory | 433/39 |
| 1,661,068 | A * | 2/1928 | Gaillard | 433/158 |
| 1,908,145 | A * | 5/1933 | Harper | 433/158 |
| 2,043,999 | A * | 6/1936 | Harper | 433/158 |
| 2,090,904 | A | 8/1937 | Singer | |
| 2,611,182 | A | 9/1952 | Tofflemire | |
| 3,108,377 | A | 10/1963 | Meyer | |
| 3,842,505 | A | 10/1974 | Eames | |
| 3,890,714 | A | 6/1975 | Gores | |
| 4,024,643 | A | 5/1977 | Eisenberg | |
| 4,259,070 | A | 3/1981 | Soelberg et al. | |
| 4,337,041 | A | 6/1982 | Harsany | |
| 4,396,374 | A * | 8/1983 | Ericson | 433/39 |
| 4,449,928 | A * | 5/1984 | von Weissenfluh | 433/40 |
| 4,468,199 | A | 8/1984 | Weikel | |
| 4,523,909 | A | 6/1985 | Lazarus | |
| 4,536,155 | A | 8/1985 | Ireland | |
| 4,553,937 | A | 11/1985 | Ropers | |
| 4,601,662 | A | 7/1986 | Galler | |
| 4,704,087 | A | 11/1987 | Dragan | |

(Continued)

FOREIGN PATENT DOCUMENTS

EP 0910996 A1 * 4/1999 ............... A61C 5/12
FR 2820024 A1 * 8/2002 ............... A61C 5/12

(Continued)

*Primary Examiner* — Cris L Rodriguez
*Assistant Examiner* — Mirayda A Aponte
(74) *Attorney, Agent, or Firm* — Quarles & Brady LLP

(57) ABSTRACT

A dental separator ring includes an elastic body having a first end and an opposed second end spaced from the first end. The body has three axes defined by a front to rear reference line of the body, a side to side reference line of the body, and a top to bottom reference line of the body. A first surface engager is connected to the first end of the body by a first connector, and a second surface engager is connected to the second end of the body by a second connector. The first connector allows motion of the first surface engager in all three axes, and the second connector allows motion of the second surface engager in all three axes. A third surface engager and a fourth surface engager that allow motion in all three axes may also be included in the separator ring.

20 Claims, 9 Drawing Sheets

(56) References Cited

U.S. PATENT DOCUMENTS

| | | | |
|---|---|---|---|
| 4,718,849 A | 1/1988 | von Weissenfluh et al. | |
| 4,781,583 A | 11/1988 | Lazarus | |
| 4,997,367 A | 3/1991 | Kassel | |
| 5,017,140 A | 5/1991 | Ascher | |
| 5,035,615 A | 7/1991 | Din | |
| 5,104,317 A | 4/1992 | Riazi | |
| 5,114,341 A | 5/1992 | Kassel | |
| 5,425,635 A | 6/1995 | Croll | |
| 5,460,525 A * | 10/1995 | Rashid | 433/155 |
| 5,501,595 A | 3/1996 | Brorson | |
| 5,527,181 A | 6/1996 | Rawls et al. | |
| 5,607,302 A | 3/1997 | Garrison et al. | |
| 5,622,496 A | 4/1997 | Champagne | |
| 5,626,476 A | 5/1997 | Champagne | |
| 5,730,592 A | 3/1998 | Meyer | |
| 5,807,101 A | 9/1998 | Scalzo | |
| 5,975,906 A | 11/1999 | Knutson | |
| 5,997,302 A | 12/1999 | Alpert | |
| 6,079,978 A | 6/2000 | Kunkel | |
| 6,142,778 A | 11/2000 | Summer | |
| 6,155,823 A | 12/2000 | Nagel | |
| 6,162,055 A | 12/2000 | Montgomery et al. | |
| D439,667 S | 3/2001 | Brown | |
| 6,206,697 B1 * | 3/2001 | Hugo | 433/155 |
| 6,220,253 B1 | 4/2001 | Wright | |
| 6,220,858 B1 | 4/2001 | McKenna et al. | |
| 6,234,793 B1 | 5/2001 | Brattesani et al. | |
| 6,315,566 B1 | 11/2001 | Shen et al. | |
| 6,325,625 B1 | 12/2001 | Meyer | |
| 6,350,122 B1 | 2/2002 | Meyer | |
| 6,375,463 B1 | 4/2002 | McLean et al. | |
| 6,425,760 B1 | 7/2002 | Summer et al. | |
| 6,435,874 B1 | 8/2002 | Hughes | |
| 6,439,886 B1 * | 8/2002 | Thoreson | 433/155 |
| 6,468,080 B1 | 10/2002 | Fischer et al. | |
| 6,479,592 B2 | 11/2002 | Rheinberger et al. | |
| 6,482,007 B2 | 11/2002 | Stanwich et al. | |
| 6,540,072 B1 | 4/2003 | Fischer | |
| 6,589,053 B2 * | 7/2003 | Bills | 433/139 |
| 6,599,125 B1 | 7/2003 | Freilich et al. | |
| 6,609,911 B2 * | 8/2003 | Garrison | 433/139 |
| 6,619,956 B1 | 9/2003 | Weir | |
| 6,712,608 B2 | 3/2004 | Bills | |
| 6,761,562 B2 | 7/2004 | Von Weissenfluh | |
| 6,767,955 B2 | 7/2004 | Jia | |
| 6,890,176 B2 | 5/2005 | Hahn | |
| 6,893,258 B1 | 5/2005 | Kert | |
| 6,976,841 B1 | 12/2005 | Osterwalder | |
| 7,097,364 B2 | 8/2006 | Wang | |
| 7,175,432 B2 * | 2/2007 | McDonald | 433/153 |
| 7,284,983 B2 * | 10/2007 | McDonald | 433/153 |
| 7,293,990 B2 | 11/2007 | Hirsch et al. | |
| 8,517,732 B2 * | 8/2013 | Segal et al. | 433/155 |
| 8,529,258 B2 * | 9/2013 | Doenges et al. | 433/148 |
| 8,647,120 B2 * | 2/2014 | Marteney et al. | 433/215 |
| 2002/0119424 A1 | 8/2002 | Margeas et al. | |
| 2002/0128347 A1 | 9/2002 | Blackwell et al. | |
| 2002/0155410 A1 * | 10/2002 | Bills | 433/153 |
| 2003/0069326 A1 | 4/2003 | Stangel et al. | |
| 2003/0165793 A1 | 9/2003 | Yobel et al. | |
| 2004/0053189 A1 | 3/2004 | Friedman | |
| 2004/0229186 A1 | 11/2004 | Slone | |
| 2004/0265779 A1 | 12/2004 | McDonald | |
| 2005/0074716 A1 | 4/2005 | Cleary et al. | |
| 2005/0089813 A1 | 4/2005 | Slone | |
| 2005/0089814 A1 | 4/2005 | Slone | |
| 2005/0118554 A1 * | 6/2005 | Kilcher et al. | 433/141 |
| 2005/0147941 A1 | 7/2005 | McDonald | |
| 2005/0231983 A1 | 10/2005 | Dahm | |
| 2005/0255428 A1 | 11/2005 | Coopersmith | |
| 2005/0287490 A1 | 12/2005 | Stookey et al. | |
| 2005/0287491 A1 | 12/2005 | Slone | |
| 2006/0009540 A1 | 1/2006 | Jia et al. | |
| 2006/0019217 A1 | 1/2006 | Yates | |
| 2006/0084029 A1 | 4/2006 | Viscomi et al. | |
| 2006/0088798 A1 | 4/2006 | Feinbloom et al. | |
| 2006/0110700 A1 | 5/2006 | Cipolla et al. | |
| 2006/0154197 A1 | 7/2006 | Gargiulo | |
| 2006/0155171 A1 | 7/2006 | Yang | |
| 2006/0188835 A1 | 8/2006 | Nagel et al. | |
| 2006/0275732 A1 | 12/2006 | Cao | |
| 2006/0275733 A1 | 12/2006 | Cao | |
| 2007/0148613 A1 | 6/2007 | Stoll | |
| 2007/0172793 A1 * | 7/2007 | Doenges et al. | 433/139 |
| 2008/0064009 A1 | 3/2008 | Clark | |
| 2008/0064012 A1 | 3/2008 | Clark | |
| 2012/0322026 A1 * | 12/2012 | Clark | 433/29 |
| 2013/0344455 A1 * | 12/2013 | Hull et al. | 433/29 |

FOREIGN PATENT DOCUMENTS

| | | | | |
|---|---|---|---|---|
| WO | WO 9409716 A1 * | 5/1994 | | A61C 5/12 |
| WO | WO 0149203 A1 * | 7/2001 | | |
| WO | WO 02069832 A1 * | 9/2002 | | |
| WO | WO 03065921 A1 * | 8/2003 | | |
| WO | WO 2009105279 A1 * | 8/2009 | | |

* cited by examiner

DENTAL SEPARATOR RING

CROSS-REFERENCES TO RELATED APPLICATIONS

This application claims priority from U.S. Provisional Patent Application No. 61/615,648, filed Mar. 26, 2012.

STATEMENT REGARDING FEDERALLY SPONSORED RESEARCH

Not Applicable.

BACKGROUND OF THE INVENTION

1. Field of the Invention

The present invention relates to a dental separator ring that may be used in methods for the restoration of a decayed portion of a tooth.

2. Description of the Related Art

Dental cavities that have spread to the dentin or have undergone cavitation are typically treated by removing the decayed portion of the tooth and thereafter filling the missing tooth structure with a restorative material such as silver (amalgam), white (polymeric resin), porcelain, or gold. Cavities that are located adjacent to neighboring teeth are called interproximal cavities.

When treating interproximal cavities, the dentist first removes the decayed portion of the side of the tooth. In order to properly deposit the restorative material on the side of the tooth without undesired leaking of the restorative material beyond the side of the tooth, the dentist places a dental matrix around at least a portion of the tooth. The dental matrix may be a metallic or plastic strip, and when the matrix is placed around at least a portion of the tooth, the matrix acts as a form for the desired shape of the restored tooth. Various dental matrices and methods are shown in U.S. Patent Application Publication Nos. 2008/0064012 and 2008/0064003. (These patents and all other patents and publications cited herein are incorporated herein by reference.)

A dental separator ring may also be used when filling interproximal cavities. The separator ring applies pressure against the adjacent teeth to force the adjacent teeth apart to allow a dental matrix to be positioned between the adjacent teeth. The dental separator ring may also include specially configured ends that also function as a matrix stabilizer that maintains the matrix and any other matrix stabilizer in a desired position with respect to the tooth to be restored. Example dental separator rings can be found in U.S. Pat. Nos. 7,284,983, 6,325,625, 6,206,697 and 5,607,302 and U.S. Patent Application Publication Nos. 2008/0064009, 2007/0172793 and 2005/0147941.

The device of U.S. Pat. No. 7,284,983 has disadvantages. For example, the wedge shaped engager can make a flat spot when more of the tooth is missing. Another concern is that the angle of pressure may be less separating mesial-distal (front-back) and more buccal-lingual which will not spread the teeth as much.

The device of U.S. Pat. No. 5,607,302 also has disadvantages. For example, the sharp point on the mid-interproximal runs into the dental matrix and can make a flat spot. Also, the device focuses pressure in the middle between occlusal and gingival. Additionally, the pointed and arcing area in general encroaches in the interproximal area and will not allow the dental matrix to expand fully from buccal to lingual so as to reach out and create a solid contact on a tough contact or diastema case. Thus, the device does not allow the whole matrix to arc out. The resultant marginal ridge/contact area can be unhygienic. It will also be prone to fracture because it is too narrow from buccal to lingual, first because of the reduction in total volume of composite filling material, and secondly because the protection (buttressing) of the neighboring marginal ridge is not fully utilized. Also, the shape of the device can smash a traditional wedge.

Therefore, although various dental separator rings are available, there is still a need for an improved dental separator ring that may be used in the restoration of a decayed portion of a tooth.

SUMMARY OF THE INVENTION

The separator ring of the invention can be used in a method for the restoration of a tooth having an original shape including a top surface and an interproximal surface. In the method, a portion of the top surface of the tooth and a portion of the interproximal surface of the tooth are removed using conventional dental instruments to form a hollow cavity preparation that extends from the top surface to the interproximal surface of the tooth. The hollow cavity preparation is preferably saucer shaped wherein the cavity preparation does not extend inward more than two millimeters from the interproximal surface of the tooth. The removed portion of the interproximal surface of the tooth is then surrounded with a sectional translucent (preferably transparent) anatomic dental matrix. An interproximal matrix stabilizer may also be used to hold the dental matrix against the tooth. See, for example, U.S. Patent Application Publication No. 2008/0064012.

The invention provides an improved dental separator ring that can be used in this type of restoration method. The dental separator ring can separate teeth and/or create adaptation pressure on an interproximal dental matrix stabilizer and/or a dental matrix. In one form, the separator ring includes an elastic body that terminates in four Independently hinged surface engagers. The surface engagers are dimensioned to separate teeth and/or create adaptation pressure on an interproximal dental matrix stabilizer and/or a dental matrix.

In one non-limiting example form, one or more of the four independently hinged surface engagers include notches or material weaknesses between sections ("talons") of the surface engagers. The notches or material weaknesses allow the engagers to adapt to a variety of tooth shapes and tooth alignments. Preferably, all four of the independently hinged surface engagers include notches or material weaknesses between sections ("talons") of the surface engagers.

Therefore, it is an advantage of the invention to provide an improved dental separator ring for separating teeth and/or for creating adaptation pressure on an interproximal dental matrix stabilizer and/or a dental matrix.

It is another advantage of the invention to provide an improved dental separator ring that includes an elastic body that terminates in independently hinged surface engagers. The independent adapting hinging areas allow control of flow and endpoint of restoration composite placement to eliminate excesses (overhangs) in the same manner as a dental wedge, specifically at line angle areas at the gingival corners of the restorations where overhangs are common and extremely difficult to remove because of poor access and poor visualization.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
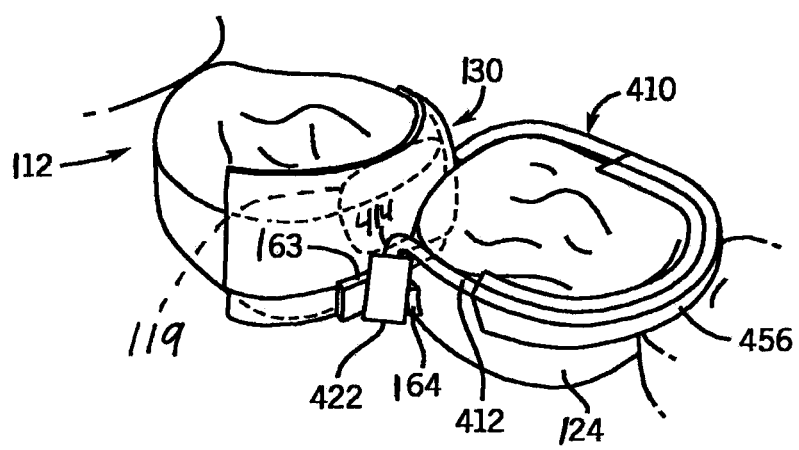
FIG. 1 is a top perspective view of a prior art dental separator ring.
Figure 2:
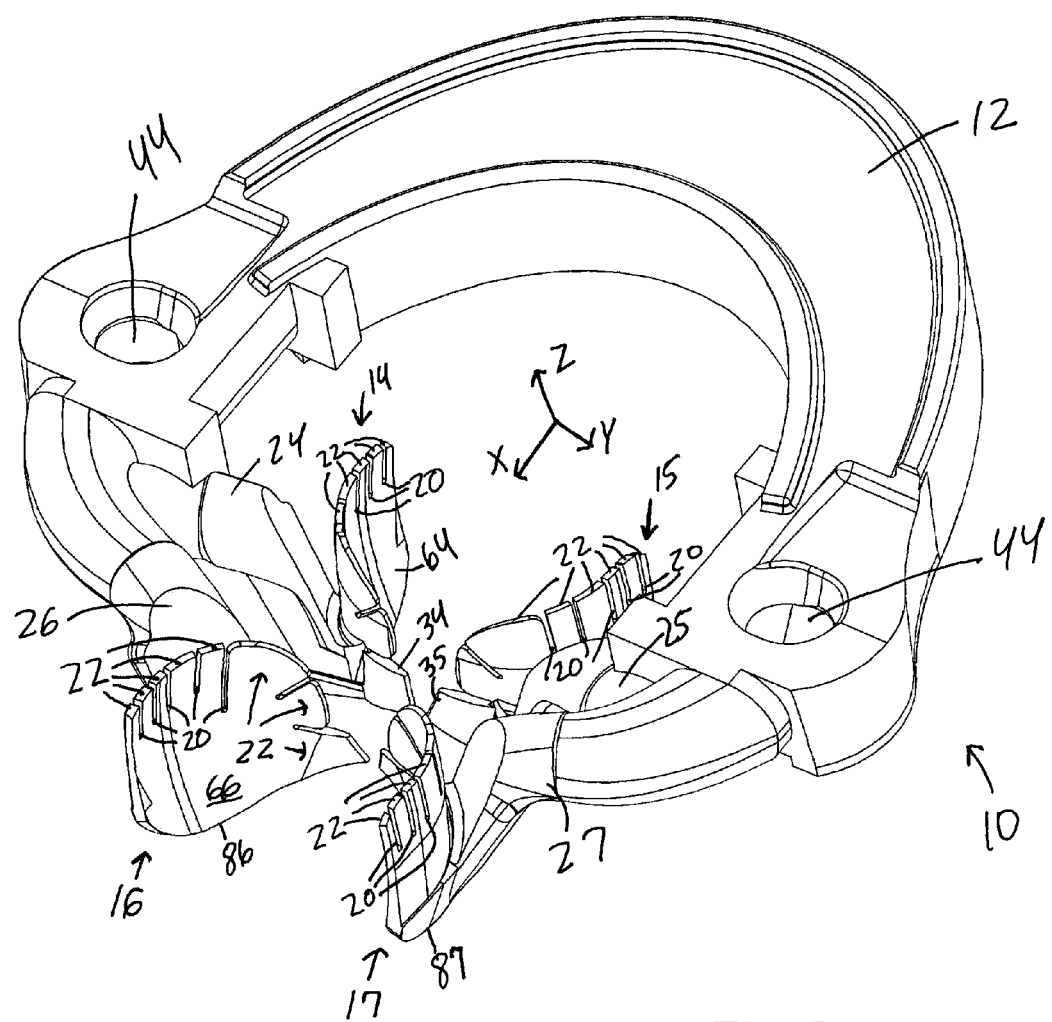
FIG. 2 is top perspective view of an example embodiment of a dental separator ring according to the invention.
Figure 3:
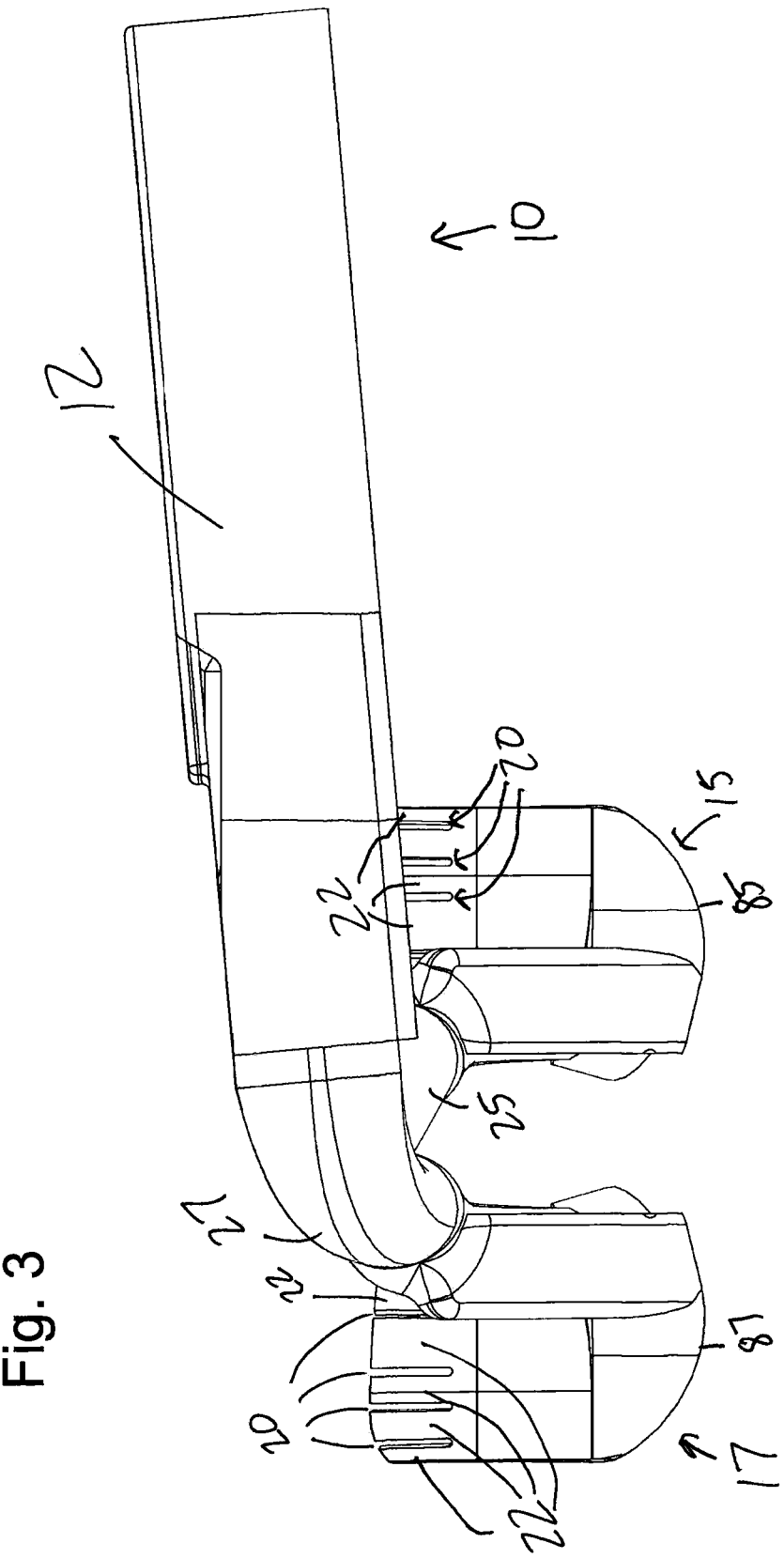
FIG. 3 is a right elevational view of the separator ring of FIG. 2, the left elevational view being a mirror image thereof.
Figure 4:
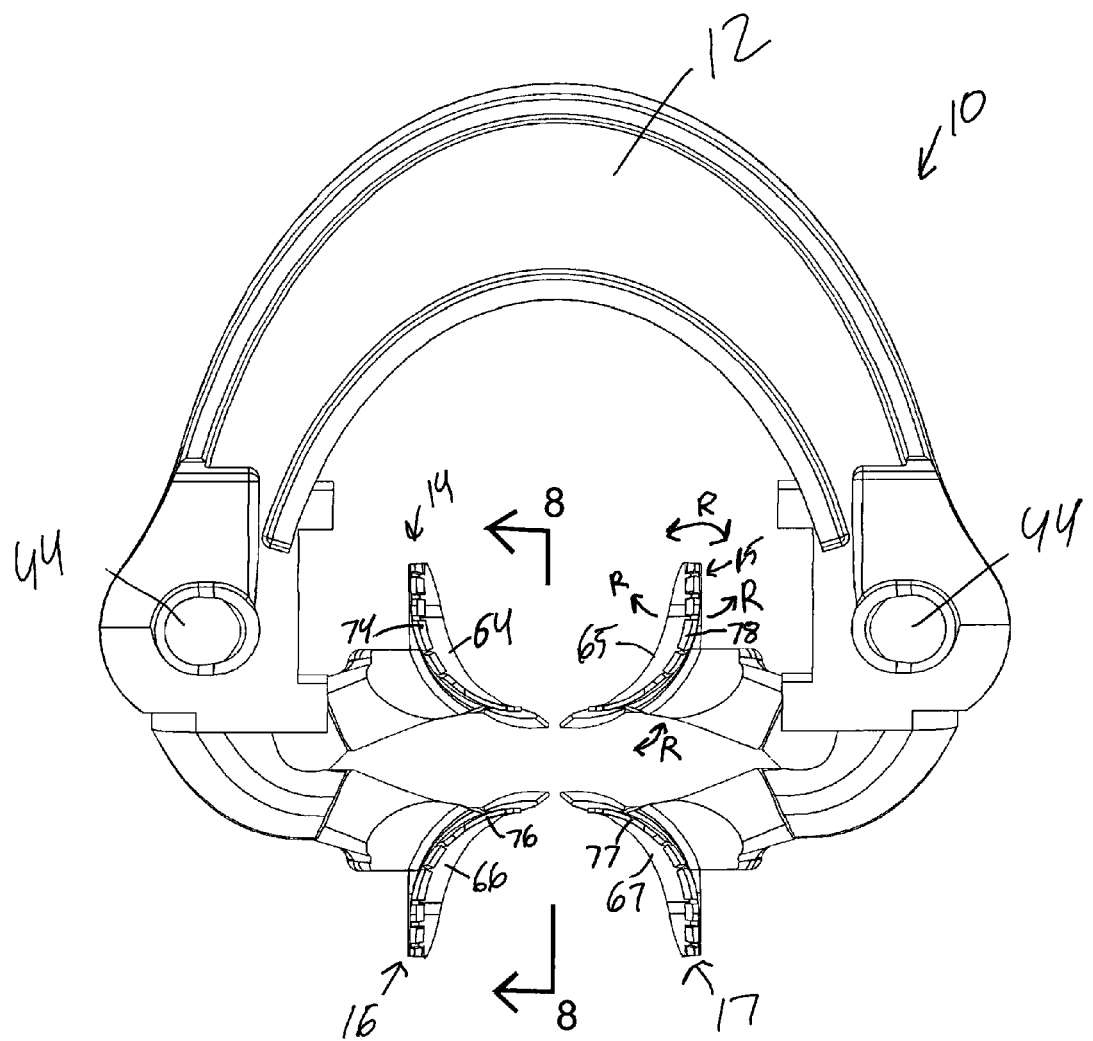
FIG. 4 is a top plan view of the separator ring of FIG. 2.
Figure 5:
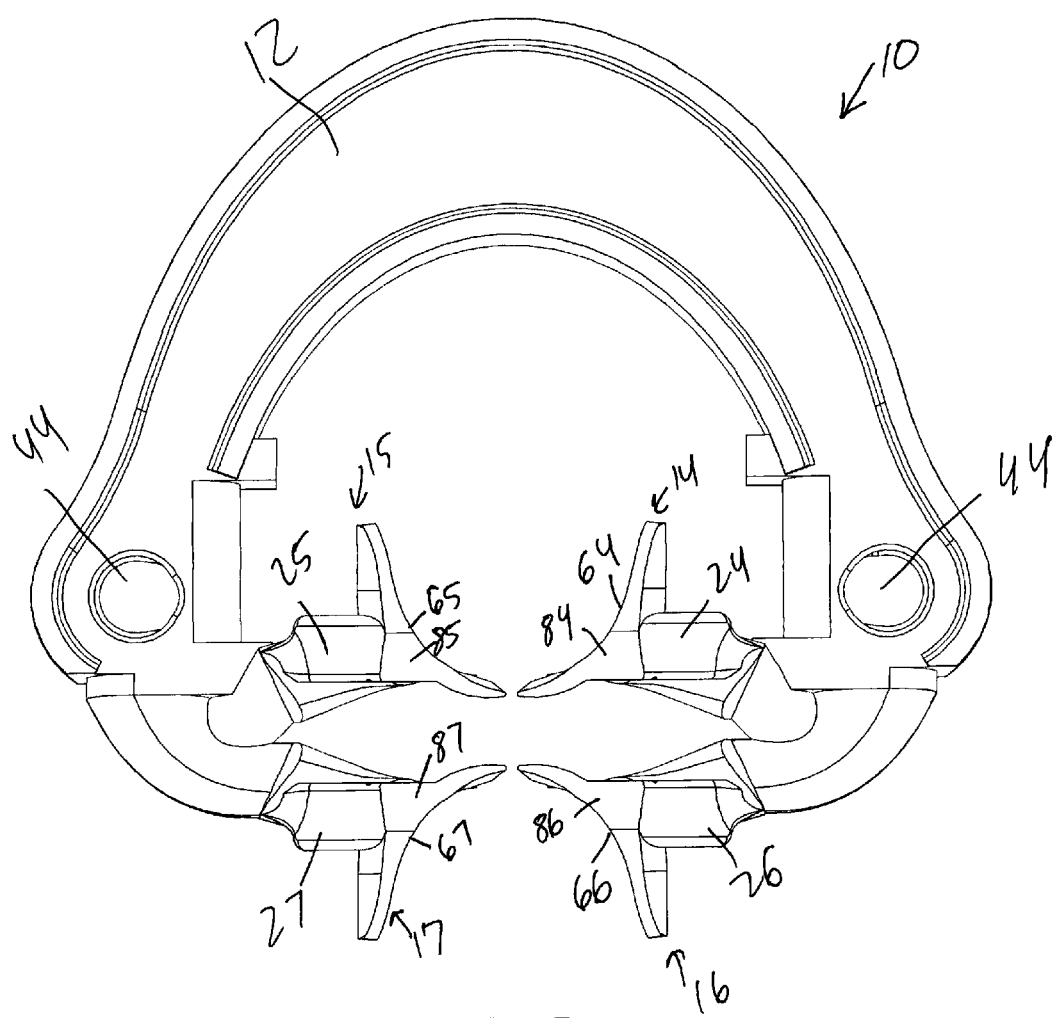
FIG. 5 is a bottom view of the separator ring of FIG. 2.
Figure 6:
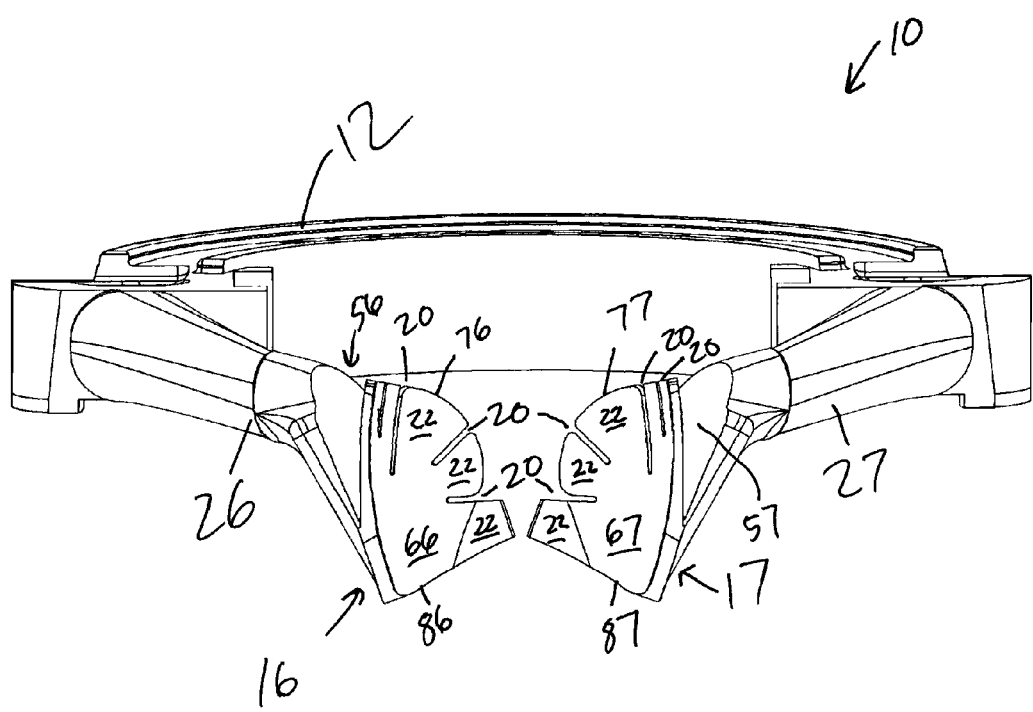
FIG. 6 is a front elevational view of the separator ring of FIG. 2.
Figure 7:
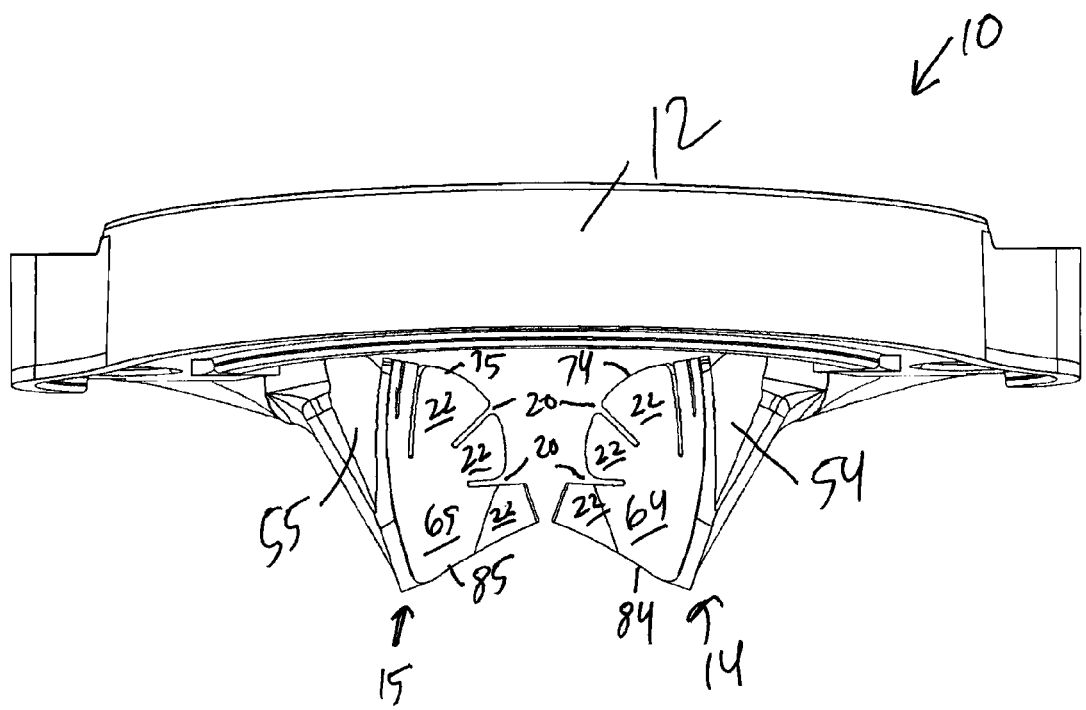
FIG. 7 is a rear elevational view of the separator ring of FIG. 2.
Figure 8:
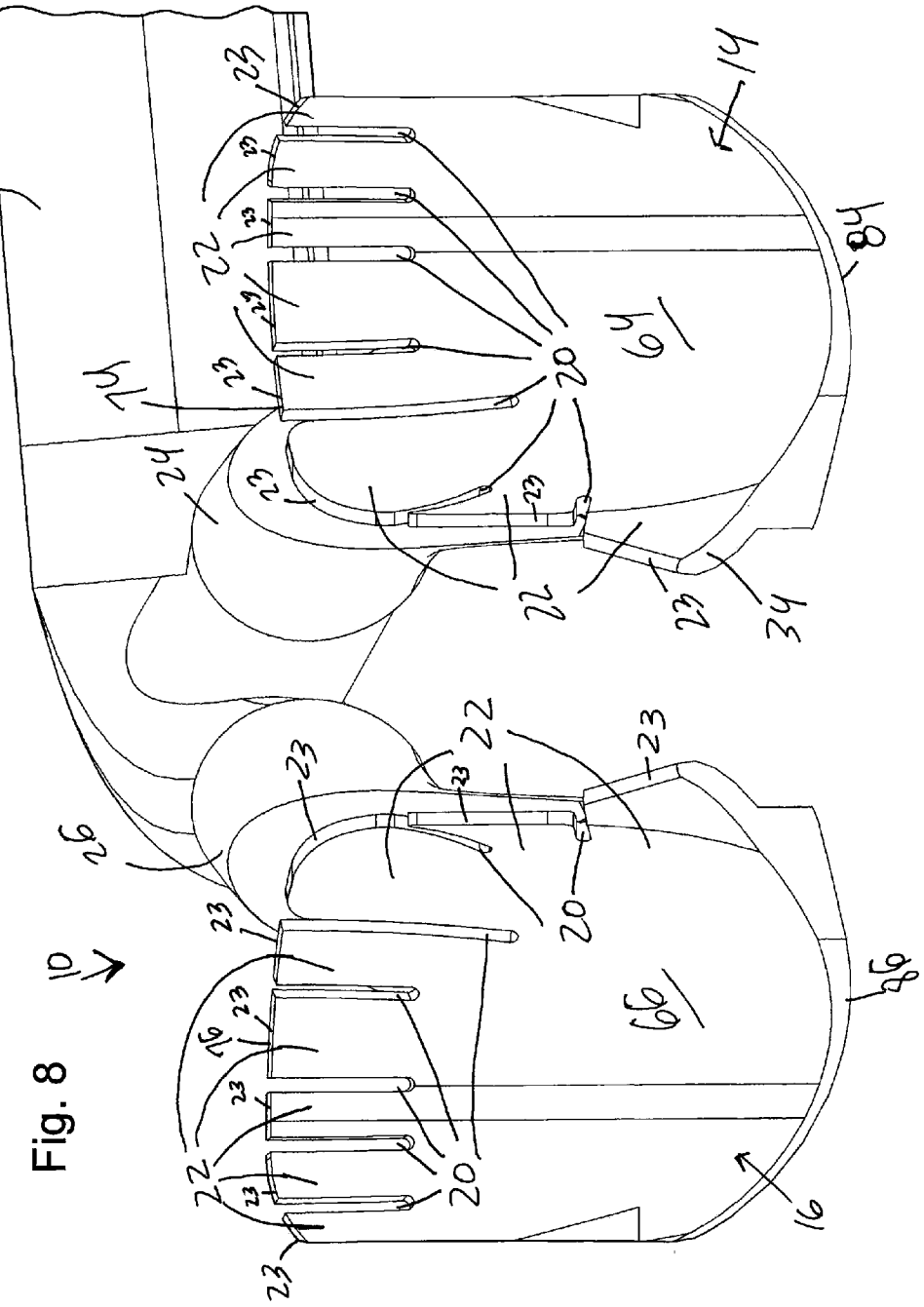
FIG. 8 is a cross-sectional view of the separator ring of FIG. 2-7 taken along line 8-8 of FIG. 4.

In order to provide context for the present invention, FIG. 1 shows the use of prior art dental separator ring 410. After creation of a cavity preparation 119 in the tooth 112 of FIG. 1, a sectional anatomic translucent dental matrix 130 is inserted between the tooth 112 and the tooth 124 as shown in FIG. 1. The dental matrix 130 is placed around the tooth 112 maintaining anatomic root adaptation contact using an interproximal dental matrix stabilizer having separate end members 163, 164. A dental separator ring 410 is then placed in the interproximal embrasure to create slight tooth separation and additional adaptation pressure on the separate end members 163, 164 of the interproximal dental matrix stabilizer and/or the dental matrix 130. The separator ring 410 has an arcuate body 412 having a first leg 414 and a second leg (not shown) that extend at a generally right angle from the body 412. The separator ring 410 has a clamp 422 mounted on the end of the leg 414, and a similar clamp (not shown) mounted on the end of the other leg (not shown). The separator ring 410 also has an arcuate cover 456. The clamp 422 of the separator ring 410 can be placed between the separate end members 163, 164 of the dental matrix stabilizer when the separator ring 410 is placed on the dental matrix stabilizer. The other clamp (not shown) of the separator ring 410 can also be placed between the opposite side end members of the dental matrix stabilizer in a similar fashion. The separator ring 410 can be used to separate teeth 112, 124 (when a matrix and matrix stabilizer are not used), or to create adaptation pressure on a matrix (when a matrix stabilizer is not used), or to create adaptation pressure on an interproximal dental matrix stabilizer and dental matrix (when a matrix and a matrix stabilizer are both used as in FIG. 1).

Turning now to FIGS. 2-9, there is shown a non-limiting example embodiment of a dental separator ring 10 according to the invention. The separator ring 10 has a curved body 12 having four independently hinged surface engagers 14, 15, 16, 17. The surface engagers 14, 15, 16, 17 are dimensioned to separate teeth and/or create adaptation pressure on an interproximal dental matrix stabilizer and/or a dental matrix. The surface engagers 14, 15, 16, 17 have a high flexibility that allows the surface engagers 14, 15, 16, 17 to engage, for example: (i) four surfaces on two adjacent teeth, or (ii) the surface of a dental matrix on one tooth and two surfaces on an adjacent tooth, or (iii) the surface of one dental matrix on one tooth and the surface of another dental matrix on an adjacent tooth, or (iv) the surface of an interproximal dental matrix stabilizer on one or both adjacent teeth. It can be appreciated that the surfaces engaged by the surface engagers 14, 15, 16, 17 can be any combination of tooth surfaces and/or matrix surfaces and/or interproximal dental matrix stabilizer surfaces. One problem with prior dental separator rings is that the low flexibility on the tooth engaging elements does not allow the ring to engage all tooth surfaces when the ring is used between bicuspids and molars. The present invention solves this problem with prior separator rings by way of the surface engagers 14, 15, 16, 17.

The four independently hinged surface engagers 14, 15, 16, 17 include notches or material weaknesses 20 between eight sections 22 ("talons") of the surface engagers 14, 15, 16, 17. The notches or material weaknesses 20 allow the sections 22 of the surface engagers 14, 15, 16, 17 to adapt to a variety of tooth shapes and tooth alignments. Looking at FIG. 8, the distal end 23 of each of the sections 22 of the surface engagers 14, 15, 16, 17 can have a decreased thickness or other material weakness to limit the pressure on a dental matrix from the distal end region of the sections 22. Although eight sections 22 are shown, the surface engagers 14, 15, 16, 17 can have different numbers of sections 22. For example, two to twelve sections 22 may be provided on each of the surface engagers 14, 15, 16, 17.

Each of the four surface engagers 14, 15, 16, 17 is connected to the body 12 by a torsion bar connector 24, 25, 26, 27 that allows each surface engager 14, 15, 16, 17 to adapt in all three axis, X, Y and Z (see FIG. 2) when engaging a tooth and/or a matrix stabilizer and/or a dental matrix. Torsion bar connectors 24, 26 are connected to a first end 13a of the body 12, and torsion bar connectors 25, 27 are connected to a second end 13b of the body 12 (see FIG. 9). Each torsion bar connector 24, 25, 26, 27 can be round in cross section allowing easier pliability for torsion ease. Note the rotation arrows R in FIG. 8. Spaces 54, 55, 56, 57 are provided between the four surface engagers 14, 15, 16, 17 and the torsion bar connectors 24, 25, 26, 27 respectively. The spaces 54, 55, 56, 57 provide space for flexing of the sections 22 toward the torsion bar connectors 24, 25, 26, 27. The four independently hinged surface engagers 14, 15, 16, 17 include concave surfaces 64, 65, 66, 67 extending between a first side 74, 75, 76, 77 and an opposed second side 84, 85, 86, 87 of each of the surface engagers 14, 15, 16, 17, respectively.

Sections 22 of the bottom surface engagers 14, 15 are designed as strongest and specifically positioned to apply the greatest force at the buccal-gingival line angle and linguo-gingival line angle. As detailed above, prior devices applied too much of the pressure in the middle between occlusal and gingival.

Sections 22 of the bottom surface engagers 14, 15 are designed to also interface with a dental wedge (such as that shown in U.S. Patent Application Publication No. 2011/0171596) to create a continuous seal from wedge pressure to talon pressure. Previous separators either had a simple point contact or a broader but more coronal contact that did not specifically focus on preventing surplus composite from flowing past the line angle margins leading to overhangs and leaking areas where the excess composite is not properly bonded to the tooth. The bottom surface engagers 14, 15 include protrusions 34, 35, respectively, to create this continuous seal. The protrusions 34, 35 (which are somewhat shaped like a sector of a circle) can fit between a dental wedge and dental matrix to limit leakage of composite at the bottom of the matrix. The top surface engagers 16, 17 could include similar protrusions.

Figure 9:
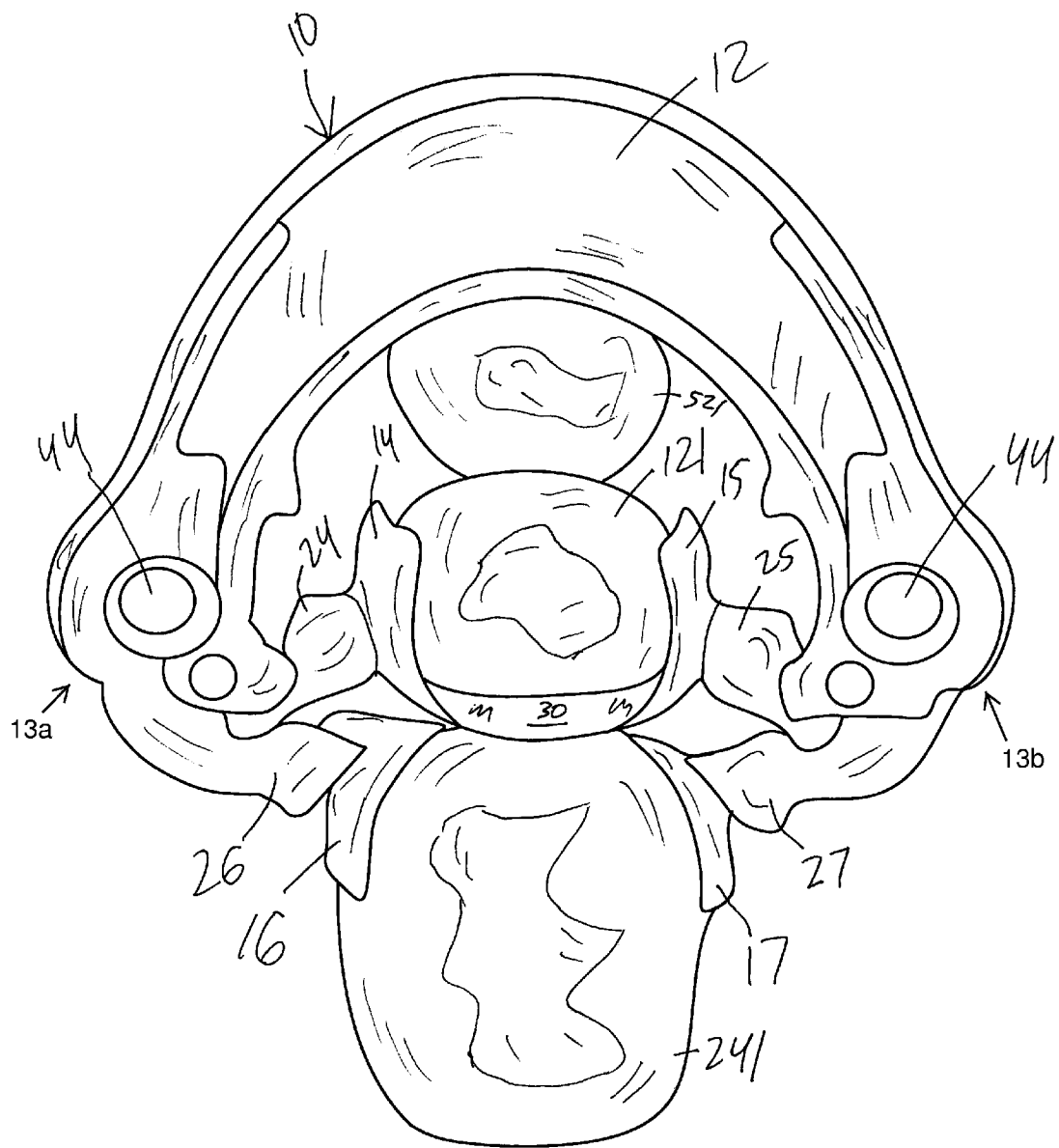
FIG. 9 is a top plan view of the separator ring of FIG. 2 engaging adjacent teeth.

The dental separator ring 10 can be placed with a traditional separator forceps or a rubber dam forceps using openings 44 in the body 12. FIG. 9 shows surface engagers 14, 15, 16, 17 of the separator ring 10 engaging adjacent teeth 121 and 241 and matrix 30. The body 12 of the separator ring 10 is above tooth 521.

Any part of the dental separator ring 10 or the entire dental separator ring 10 can be translucent or transparent (clear) allowing for light transmission during curing of a light-cured dental composite filling material. For example, the surface engagers 14, 15, 16, 17 can be translucent or transparent, and the body may be metallic. The dental separator ring 10 can be molded from a translucent or transparent polymeric material with or without a spring metal in the body 12. Without the spring metal, the ring 10 is less expensive to make and could be sold as a single use item. Thus, the dental separator ring 10 can be manufactured as an over-molded part (e.g., resin over a metal, such as titanium or spring steel), or one with straight polymeric resin. The use of a single resin for the dental separator ring 10 can provide even pressure without indenting a dental matrix.

Although the invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A separator ring for separating teeth and/or for creating adaptation pressure on an interproximal dental matrix stabilizer and/or a dental matrix, the separator ring comprising:
    an elastic body having a first end and an opposed second end spaced from the first end;
    a first surface engager connected to the first end of the body by a first connector, the first connector allowing motion of the first surface engager in all three axes; and
    a second surface engager connected to the first end of the body by a second connector,
    wherein the first surface engager is independently hinged to the body, and the second surface engager is independently hinged to the body.

2. The separator ring of claim 1 wherein:
    the second connector allows motion of the second surface engager in all three axes.

3. The separator ring of claim 2 wherein:
    the first surface engager includes a first concave surface facing away from the first end of the body, and
    the second surface engager includes a second concave surface facing away from the first end of the body.

4. The separator ring of claim 1 wherein:
    the first connector is a first torsion bar connector, and
    the second connector is a second torsion bar connector.

5. The separator ring of claim 4 wherein:
    the first torsion bar connector is round in cross section, and
    the second torsion bar connector is round in cross section.

6. A separator ring for separating teeth and/or for creating adaptation pressure on an interproximal dental matrix stabilizer and/or a dental matrix, the separator ring comprising:
    an elastic body having a first end and an opposed second end spaced from the first end;
    a first surface engager connected to the first end of the body by a first connector, the first connector allowing motion of the first surface engager in all three axes; and
    a second surface engager connected to the second end of the body by a second connector,
    wherein the first surface engager includes a first side and an opposed second side, the first side of the first surface engager including a plurality of spaced apart flexing sections, and
    wherein the first surface engager includes a notch between adjacent spaced apart flexing sections, and
    wherein notches face away from gingival when the separator ring is positioned to separate the teeth.

7. The separator ring of claim 6 wherein:
    the first surface engager includes a first protrusion extending away from the second side.

8. The separator ring of claim 6 wherein:
    the first surface engager includes a material weakness between adjacent spaced apart flexing sections.

9. The separator ring of claim 6 wherein:
    a distal end of one or more of the plurality of spaced apart flexing sections has a decreased thickness with respect to an opposite end of the one or more of the plurality of spaced apart flexing sections.

10. The separator ring of claim 6 wherein:
    a distal end of one or more of the plurality of spaced apart flexing sections has a material weakness with respect to an opposite end of the one or more of the plurality of spaced apart flexing sections.

11. The separator ring of claim 6 wherein:
    the second surface engager includes a first side and an opposed second side, the first side of the second surface engager including a plurality of spaced apart flexing sections.

12. The separator ring of claim 11 wherein:
    the second surface engager includes a notch between adjacent spaced apart flexing sections.

13. The separator ring of claim 12 wherein:
    notches face away from gingival when the separator ring is positioned to separate the teeth.

14. The separator ring of claim 6 wherein:
    the second surface engager includes a material weakness between adjacent spaced apart flexing sections.

15. A separator ring for separating teeth and/or for creating adaptation pressure on an interproximal dental matrix stabilizer and/or a dental matrix, the separator ring comprising:
    an elastic body having a first end and an opposed second end spaced from the first end;
    a first surface engager connected to the first end of the body by a first connector, the first connector allowing motion of the first surface engager in all three axes; and
    a second surface engager connected to the second end of the body by a second connector;
    a third surface engager connected to the first end of the body by a third connector, the third connector allowing motion of the third surface engager in all three axes; and
    a fourth surface engager connected to the second end of the body by a fourth connector, the fourth connector allowing motion of the fourth surface engager in all three axes,
    wherein,
    the first surface engager is independently hinged to the body,
    the second surface engager is independently hinged to the body,
    the third surface engager is independently hinged to the body, and
    the fourth surface engager is independently hinged to the body.

16. The separator ring of claim 15 wherein:
    the third surface engager includes a third concave surface facing away from the first end of the body, and
    the fourth surface engager includes a fourth concave surface facing away from the second end of the body.

17. The separator ring of claim 15 wherein:
- the third surface engager includes a first side and an opposed second side, the first side of the third surface engager including a plurality of spaced apart flexing sections, and
- the fourth surface engager includes a first side and an opposed second side, the first side of the fourth surface engager including a plurality of spaced apart flexing sections.

18. The separator ring of claim 15 wherein:
- each of the first surface engager, the second surface engager, the third surface engager and the fourth surface engager is adapted to independently engage a different surface area.

19. The separator ring of claim 15 wherein:
- the first surface engager and the second surface engager are adapted to independently engage different surface areas of a first tooth, and
- the third surface engager and the fourth surface engager are adapted to independently engage different surface areas of a second tooth.

20. The separator ring of claim 15 wherein:
- when the separator ring is positioned to separate the teeth, the hinged first surface engager, the hinged second surface engager, the hinged third surface engager, and the hinged fourth surface engager allow control of flow and endpoint of dental composite placement on a tooth to eliminate excesses at line angle areas at gingival corners of a dental restoration of the tooth.

\* \* \* \* \*